US009386751B2

(12) United States Patent
Creekmore

(10) Patent No.: US 9,386,751 B2
(45) Date of Patent: Jul. 12, 2016

(54) APPARATUS, SYSTEM AND METHOD FOR PRODUCING FUNGI FOR USE IN A ECOSYSTEM

(71) Applicant: Donnie Lee Creekmore, Modesto, CA (US)

(72) Inventor: Donnie Lee Creekmore, Modesto, CA (US)

( * ) Notice: Subject to any disclaimer, the term of this patent is extended or adjusted under 35 U.S.C. 154(b) by 0 days.

(21) Appl. No.: 14/080,811

(22) Filed: Nov. 15, 2013

(65) Prior Publication Data

US 2015/0366141 A1 Dec. 24, 2015

(51) Int. Cl.
*A01G 1/04* (2006.01)
*A01G 7/02* (2006.01)
*C12N 1/14* (2006.01)

(52) U.S. Cl.
CPC *A01G 1/046* (2013.01); *A01G 7/02* (2013.01); *C12N 1/14* (2013.01)

(58) Field of Classification Search
CPC .......... A01N 63/04; C12R 1/645; C12N 1/14; C12N 15/80; C12N 1/20; C12P 1/02; A01G 1/04; A01G 1/042; A01G 1/046; A01G 1/044; A01H 15/00
USPC ................................ 47/1.1; 435/254.1, 256.8
See application file for complete search history.

(56) References Cited

U.S. PATENT DOCUMENTS

| | | | | |
|---|---|---|---|---|
| 2,048,966 A * | 7/1936 | Perry | A01G 1/046 | 215/6 |
| 2,851,821 A * | 9/1958 | Guiochon | A01G 1/046 | 206/525 |
| 3,242,614 A * | 3/1966 | Thompson | A01G 1/046 | 47/1.1 |
| 3,608,709 A * | 9/1971 | Pike | B29C 65/76 | 206/219 |
| 3,865,695 A * | 2/1975 | Massier | A01G 1/046 | 435/256.8 |
| 4,027,427 A * | 6/1977 | Stoller | A01G 1/046 | 206/439 |
| 4,121,525 A * | 10/1978 | Courtis | A01H 4/001 | 111/200 |
| 4,311,477 A * | 1/1982 | Kitamura | A01G 1/046 | 206/439 |
| 4,873,195 A * | 10/1989 | Kubo | A01G 1/046 | 435/254.1 |
| 4,878,312 A * | 11/1989 | Shimizu | A01G 1/046 | 435/254.1 |
| 5,659,997 A * | 8/1997 | Sprehe | A01G 1/046 | 47/1.1 |
| 2008/0145577 A1* | 6/2008 | Bayer | A01G 1/046 | 428/35.6 |
| 2009/0307969 A1* | 12/2009 | Bayer | A01G 1/046 | 47/1.1 |

(Continued)

FOREIGN PATENT DOCUMENTS

| | | |
|---|---|---|
| JP | 04045723 A * | 2/1992 |
| JP | 05219834 A * | 8/1993 |

(Continued)

*Primary Examiner* — Son T Nguyen
(74) *Attorney, Agent, or Firm* — Steven Rinehart

(57) ABSTRACT

An apparatus, system and method for producing fungi for use in an ecosystem provides a production substrate and a spawn substrate that can be combined on demand to cultivate fungi and fungi byproducts. The substrates go through a systematic process by which they are prepared, positioned in separate sections of the vessel, sanitized, inoculated with a fungi culture, and finally combined at la later time and place demand by cutting the seal. In this manner, the shelf life is extended. The vessel is then placed inside a dispersion container, where the fungi and fungi byproducts disperse towards the ecosystem. The dispersion container comprises a container exhaust for allowing a vessel exhaust to at least partially pass through. The fungi by product directionally releases from the vessel exhaust through a vessel exhaust, such as a mesh or webbed aperture sized to release gases and extraneous liquids.

13 Claims, 7 Drawing Sheets

(56) References Cited

U.S. PATENT DOCUMENTS

Figure 1:
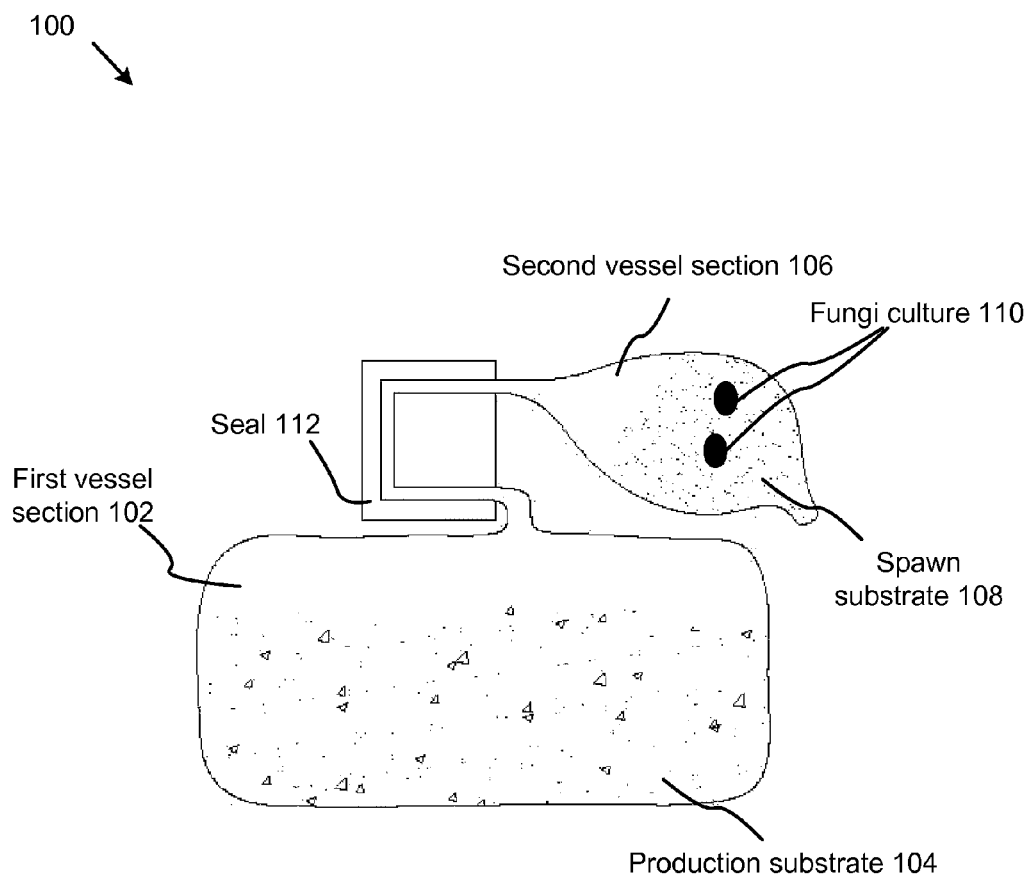
Figure 2:
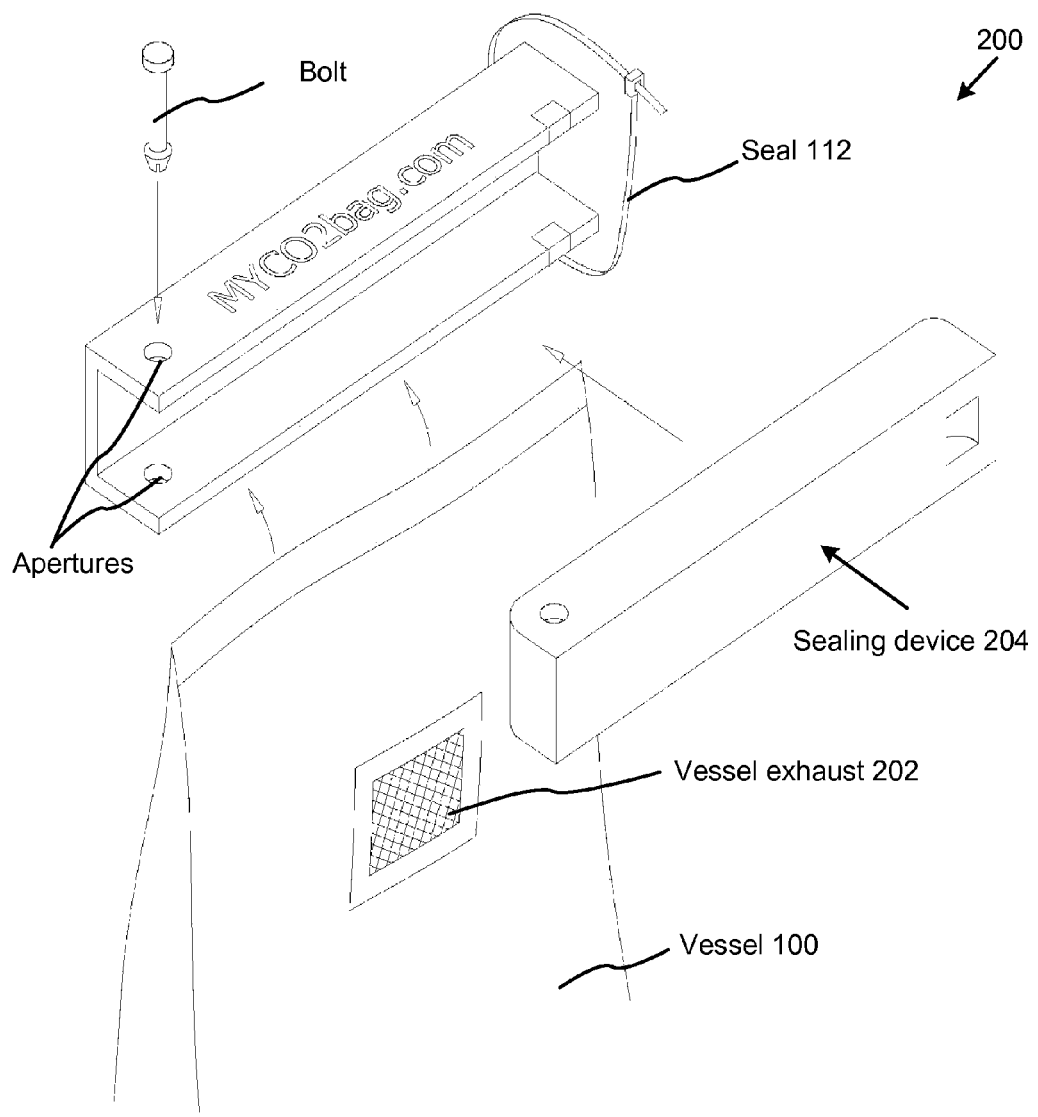
Figure 3:
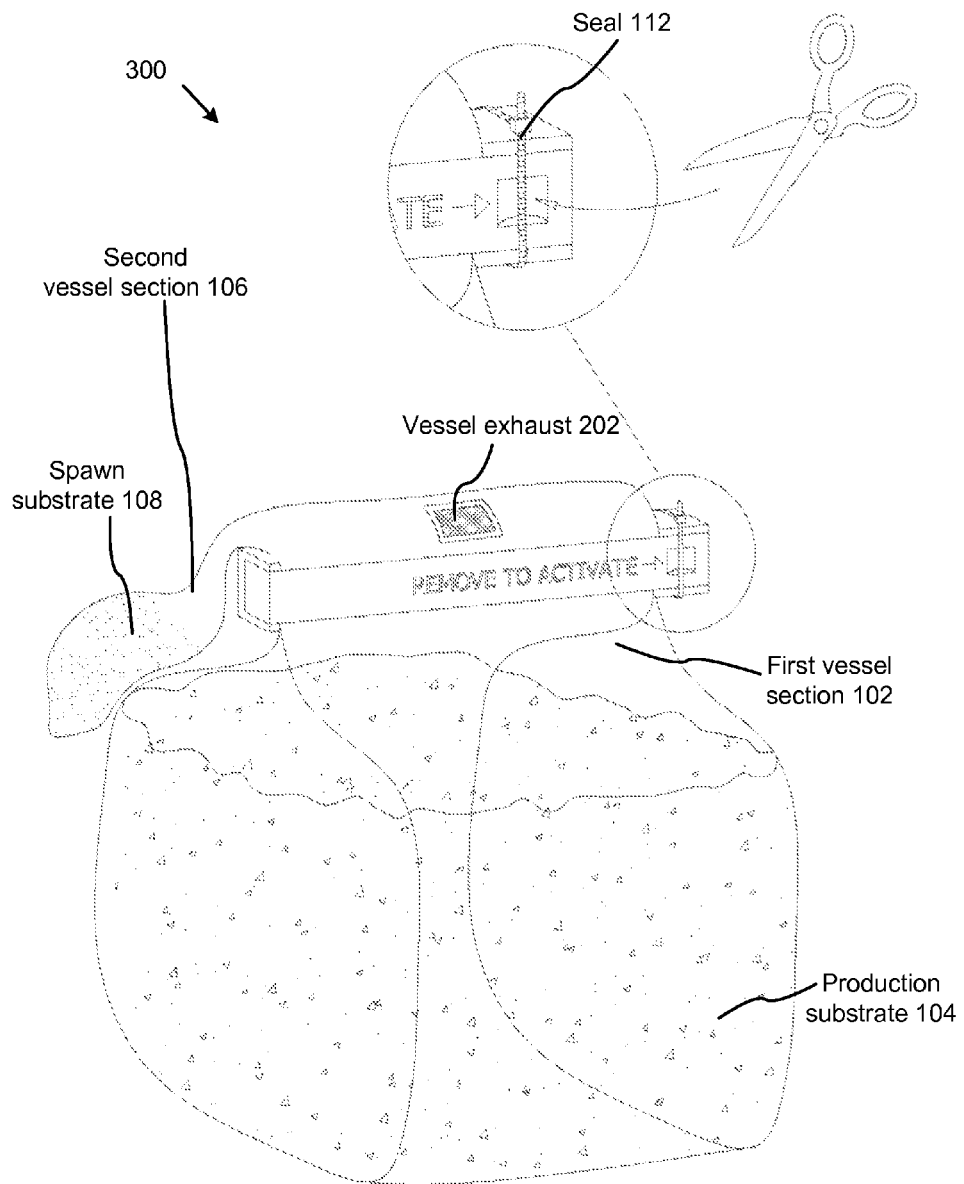
Figure 4A:
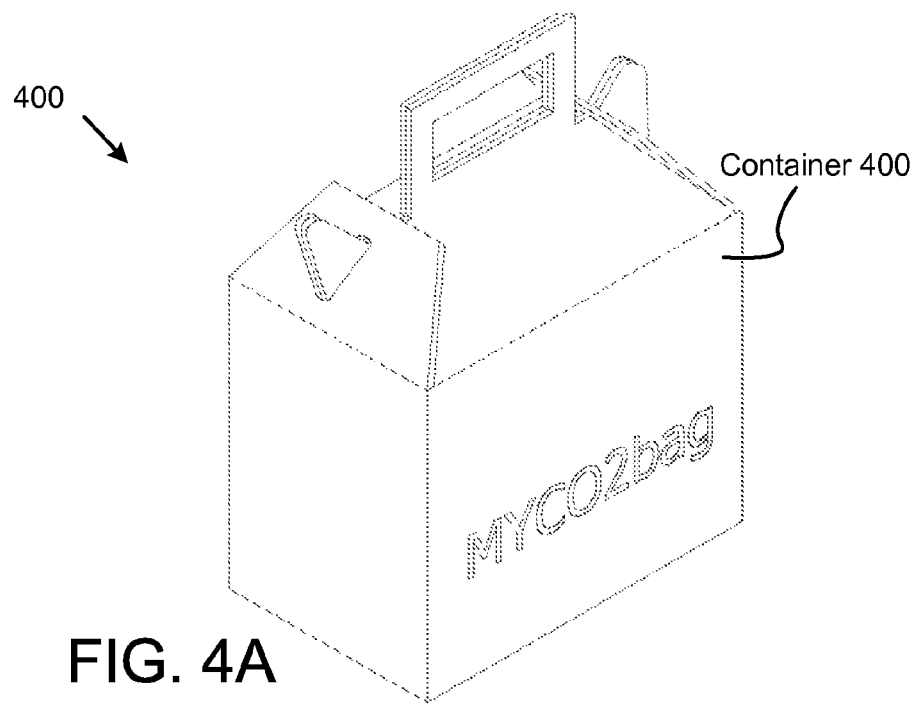
Figure 4B:
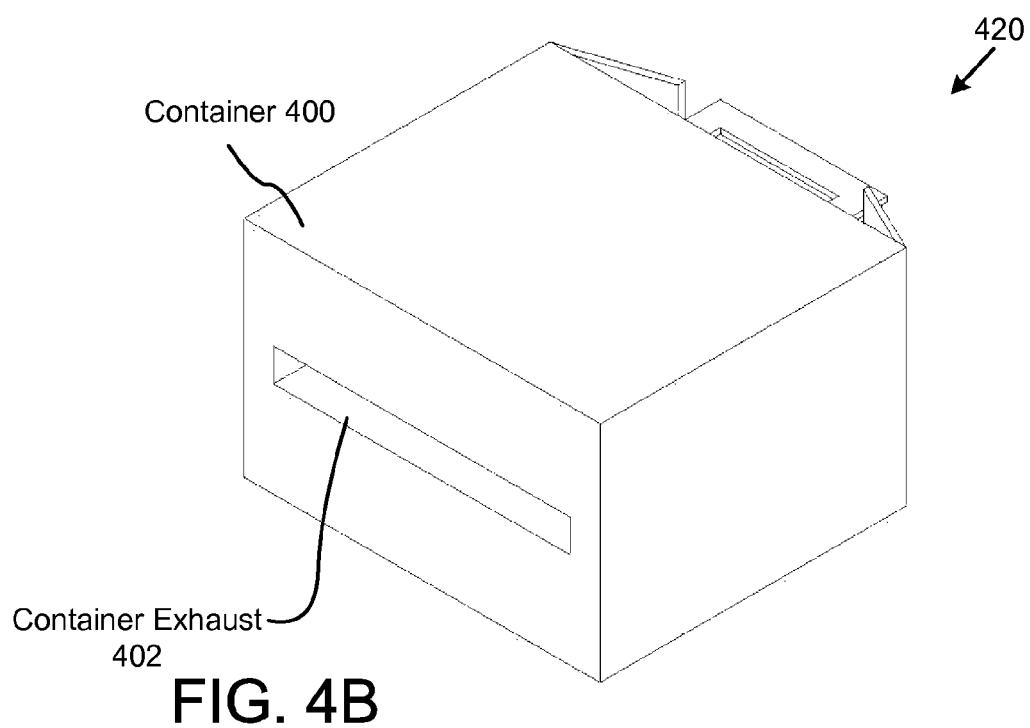
Figure 4C:
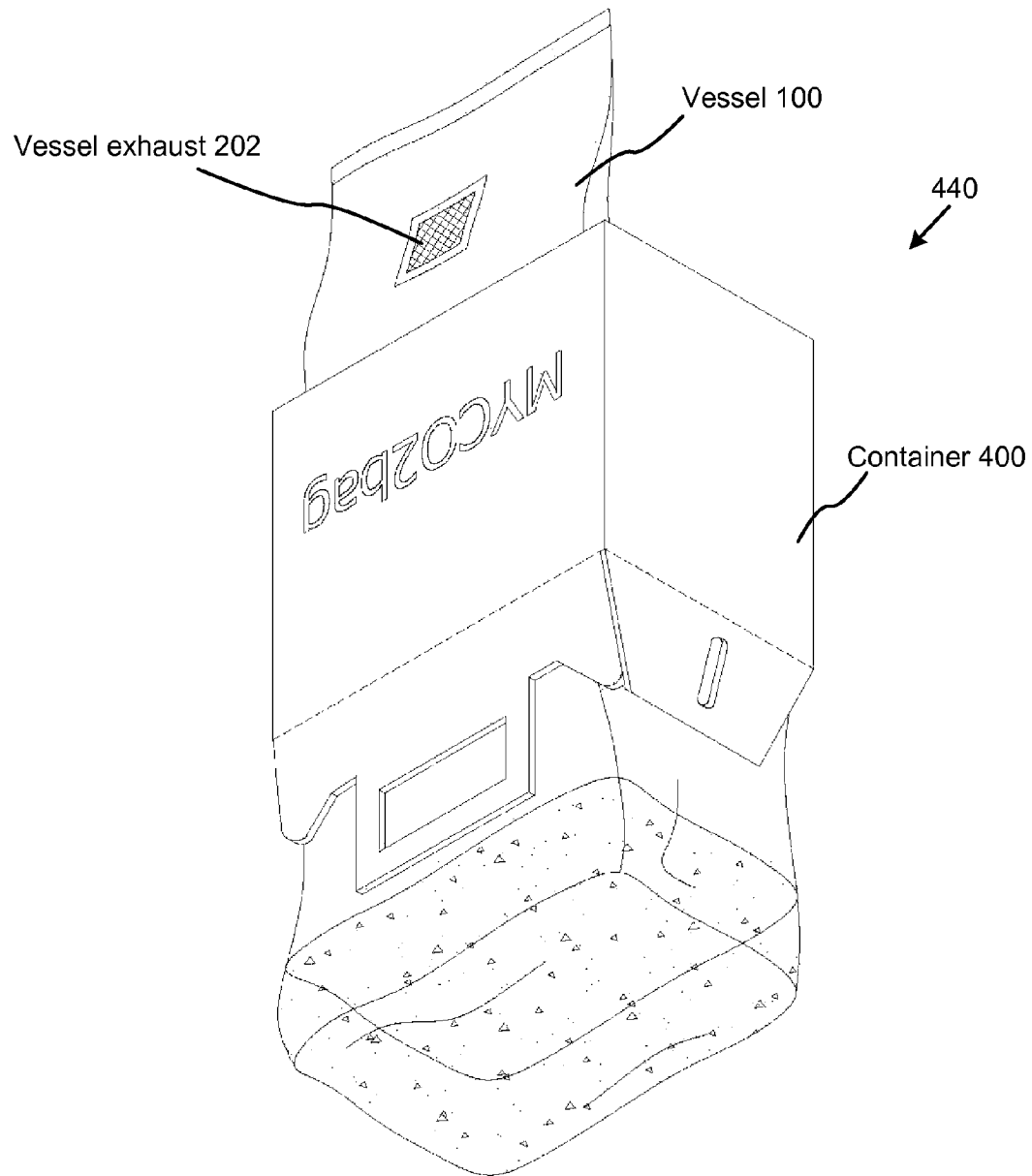

| | | | | |
|---|---|---|---|---|
| 2011/0277383 A1* | 11/2011 | Arora | ............... | A01G 1/046 47/59 S |
| 2012/0247007 A1* | 10/2012 | Verdellen | ............. | A01D 45/005 47/1.1 |
| 2014/0026260 A1* | 1/2014 | Weathers | ............... | A01G 1/046 800/298 |
| 2015/0000188 A1* | 1/2015 | Shirahane | ............... | A01G 1/046 47/1.1 |
| 2015/0250103 A1* | 9/2015 | Babcock | ................ | A01G 1/046 47/1.1 |
| 2015/0373920 A1* | 12/2015 | Babcock | ................ | A01G 7/02 47/1.1 |

FOREIGN PATENT DOCUMENTS

| | | | |
|---|---|---|---|
| JP | 05252830 A | * | 10/1993 |
| JP | 05260847 A | * | 10/1993 |
| JP | 06090621 A | * | 4/1994 |
| JP | 06141678 A | * | 5/1994 |

* cited by examiner

APPARATUS, SYSTEM AND METHOD FOR PRODUCING FUNGI FOR USE IN A ECOSYSTEM

CROSS-REFERENCES TO RELATED APPLICATIONS

This application is a continuation of, and claims priority to, U.S. Provisional Patent Application No. 61/859,172 entitled "Apparatus, System and Method for Producing Fungi for Use in an Ecosystem" and filed on Jul. 26, 2013 for Donnie Creekmore, which is incorporated herein by reference.

BACKGROUND

1. Field of the Invention

This invention relates to a system and method for producing fungi and more particularly relates to an apparatus, system and method of creating an extended shelf life for the cultivation of fungi by segregating fungi producing substrates in a vessel and combining the substrates at a desired time and place to produce fungi byproducts for the ecosystem.

2. Description of the Related Art

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

By way of educational background, a fungus is a member of a large group of eukaryotic organisms that includes microorganisms such as yeasts and molds, as well as the more familiar mushrooms. These organisms are classified in kingdom Fungi. Mushrooms are a type of fungi that need very few elements to grow. They grow best in a darker, cooler environments on a simple substrate. Mushrooms are a source of food and have many medicinal benefits. Mushrooms are also precious for ecosystems, as recyclers for wood and organic material.

An ecosystem is a community of living organisms, such as plants, animals and microbes, in conjunction with the nonliving components of their environment things like air, water and mineral soil, interacting as a system. These biotic and abiotic components are regarded as linked together through nutrient cycles and energy flows.

In many instances, mushrooms and other fungi are the only organisms that can digest the tough and fibrous lignin in wood, and make it available for other organisms. Mushroom cultivation spent substrate is very nutritive and improve soil structure. Mushrooms are also great recyclers and healers of modern society. They can grow on waste, such as coffee ground or cardboard, and some have strong soil remediation properties, such as decontaminating petroleum pollution.

Typically, a production substrate combined with a spawn substrate provides the substance that the fungus uses as food. The mycelium of the fungus grows through this kind of substrate, secreting enzymes that dissolve part of the substrate, and absorbing the nutrition that results.

Often, mushroom growing techniques require the correct combination of humidity, temperature, substrate growth medium, and starter culture. Wild harvests, outdoor log inoculation, and indoor trays all provide these elements. For example, mycelium, or actively growing mushroom culture, is placed on a substrate, usually sterilized grains such as rye or millet, and induced to grow into those grains.

Even though the above cited system and method for producing fungi for use in the ecosystem address some of the needs of the market, a method for producing fungi on demand is still desired.

SUMMARY

From the foregoing discussion, it should be apparent that a need exists for a system and method that postpones the cultivation of fungi by segregating fungi producing substrates in the same vessel, and then combining the substrates at a desired time and place for cultivation of the fungi. The need also exists for dispersing subsequently formed fungi and fungi byproducts for use in the ecosystem. In this manner, the shelf life of the fungi producing substrates may be increased, thereby allowing for greater control over the formed fungi. The present method for producing fungi provides the optimal combinations of humidity, temperature, substrate, and fungi culture for cultivating fungi on demand and directionally dispersing the fungi and fungi byproducts towards the environment and agriculture.

The present invention has been developed in response to the present state of the art, and in particular, in response to the problems and needs in the art that have not yet been fully solved by currently available fungi cultivation and fungi byproduct dispersal methods. Accordingly, the present invention has been developed to provide a method for segregating a production substrate from a spawn substrate in the same vessel, and then combining them at a desired time and place to produce fungi and fungi byproducts for dispersion into the environment and ecosystem, which may overcome many or all of the above-discussed shortcomings in the art.

In one embodiment of the present invention, a production substrates and a spawn substrate for cultivating fungi are segregated in the same vessel and then combined on demand for production of fungi and fungi byproduct. The fungi and fungi byproduct disperse towards the ecosystem through a dispersion container that holds the vessel. The substrates are initially prepared and sterilized. The substrates are then segregated to prevent premature cultivation, thereby providing a longer shelf life. After inoculating of the spawn substrate with a fungi culture, the substrates may be combined any time thereafter to initiate the cultivation of the fungi and the fungi byproduct. The vessel is placed inside a dispersion container that is configured to cultivate and enhance the production of the fungi and also to directionally disperse the fungi and fungi byproducts. A vessel exhaust that extends from a container exhaust is oriented in a desired direction for dispersion onto the ecosystem.

In some embodiments, the method may generally follow systematic series of novel steps. A first Step of the method includes preparing the production substrate. The production substrate serves as a growth medium for cultivating the fungi. A mixture of ingredients are mixed and hydrated to form the appropriate system of the production substrate. Next, the method comprises a Step of filling a vessel with the production substrate. The vessel may include a polyurethane bag, or similar transparent or opaque bag that allows light to pass through, and comprises flexibility. The production substrate is pushed off towards a section of the vessel.

The method may then proceed to a Step of sealing the vessel to form a first vessel section for the production substrate. In one embodiment, an impact seal is utilized to form the segregated first vessel section. However, the vessel may be mechanically, kinetically, or physically sealed. In yet another embodiment, a heat resistant vinyl stretch band segregates the first vessel section from the rest of the vessel.

The method then requires a Step of preparing the spawn substrate. The spawn substrate may be similar to the production substrate. Until the spawn substrate is inoculated with spawn, such as spores and mushroom mycelium, the shelf life of the spawn substrate does not commence. Next, the method comprises a Step of filling the vessel with the spawn substrate. The spawn substrate does not interact with the production substrate at this stage because the production substrate is segregated in the first vessel section of the vessel. The spawn substrate is positioned on an opposite end of the vessel, a second vessel section.

A next Step comprises sterilizing the vessel with the substrates contained inside. Those skilled in the art, in light of the present teachings, will recognize that fungi cultivation, and the substrates that produce fungi, are susceptible to contaminants, which may destroy the product. An autoclave may be utilized for sterilization. In one alternative embodiment, only the production substrate is sterilized, whereby sterilization of the vessel occurs before the spawn substrate is filled into the vessel.

A next Step includes inoculating the spawn substrate with a fungi culture, such as spores and fungi mycelium. The inoculation may utilize any inoculation procedure deemed acceptable or necessary per the growing parameters of the select fungi culture, including, without limitation, mixing by hand, or injecting with a syringe. Those skilled in the art will recognize that once inoculation of the spawn substrate occurs, it is being colonized by the select fungi culture. This creates a shelf life prior to the production substrate being inoculated. In one embodiment, the vessel may be stored at ambient room temperature not exceeding 90° Fahrenheit and not dropping below 50° Fahrenheit until the spawning substrate is completely colonized by the fungi culture.

The method may then proceed to a Step of hermetically sealing the vessel around the spawn substrate to form a second vessel section, separate from the production substrate. Like with the first vessel section, the vessel may be mechanically, kinetically, or physically sealed to form the segregated second vessel section. In one embodiment, a heat resistant vinyl stretch band segregates the second vessel section from the first vessel section and the rest of the vessel.

At the time that the fungi is needed, a Step of combining the production substrate with the spawn substrate occurs. The mechanical seal or separator rubber band is cut and the spawning substrate is mixed with the production substrate as evenly as possible without potentially compromising the permanent hermetic seal of the vessel. In some embodiments, the loose material of the mixture may be gently recompressed from the exterior of the vessel into a brick shape.

A next Step includes colonizing the production substrate with the spawn substrate. During colonization, the spawn substrate begins to decompose the production substrate and draw nutrients from the substrate mixture. Additionally, if mushroom mycelium is utilized as the fungi culture, it consolidates its hold on the production substrate by extending new strands of mycelium into the substrate mixture. The colonization produces fungi and fungi byproducts, including, without limitation, carbon dioxide, methane, nitrous oxide, liquids, and chemical extractions.

The method further comprises a Step of placing the vessel at least partially inside a dispersion container. The dispersion container also inhibits light form entering the vessel during colonization. In this manner, the dispersion container serves as a dark, cool area for efficient growth of the fungi. Those skilled in the art will recognize that fungi grow more efficiently in the dark. Additionally, the dispersion container includes a container exhaust, whereby gases from a vessel exhaust escapes.

Figure 6:
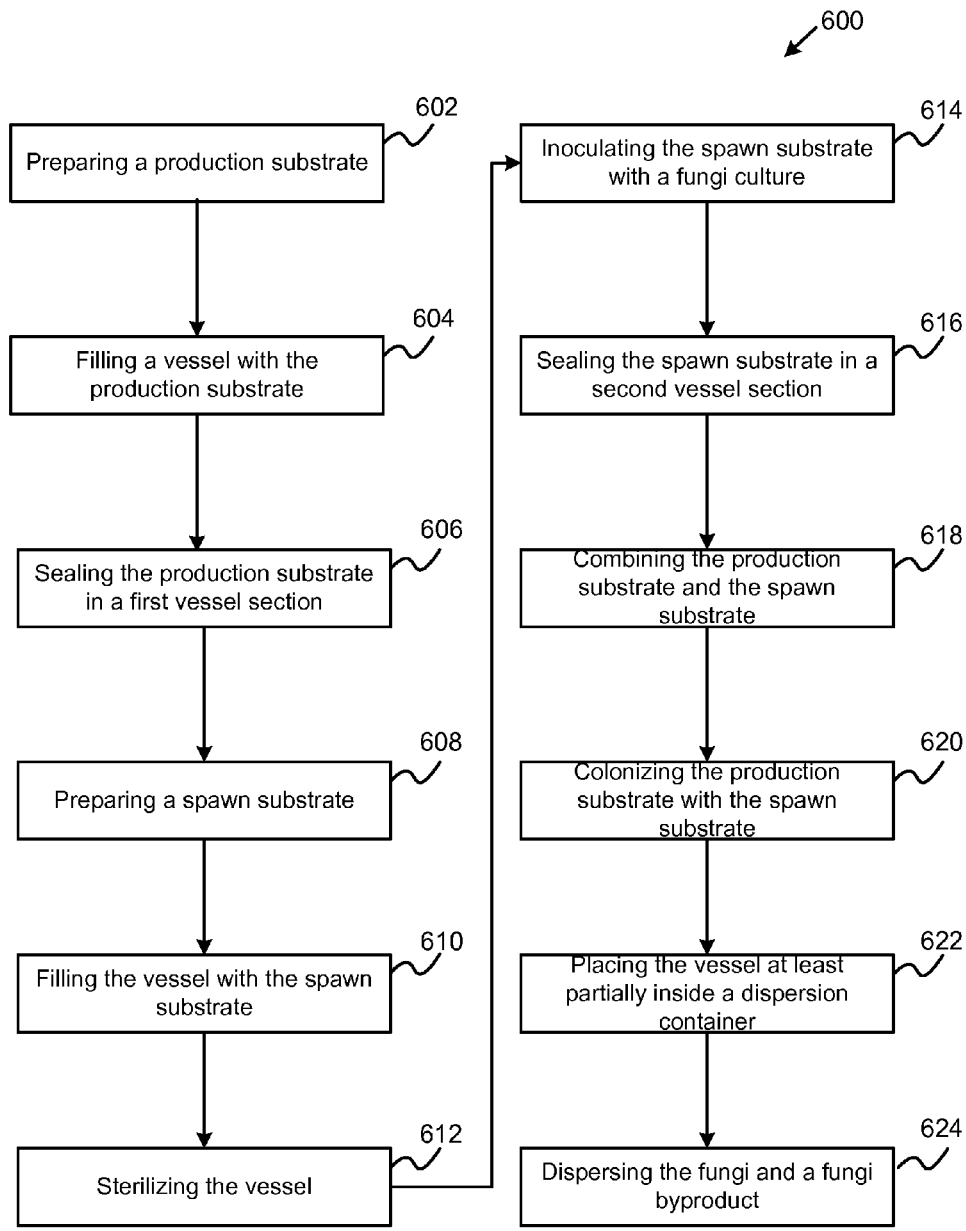

A final Step includes dispersing the fungi and the fungi byproduct for agricultural and environmental use. The dispenser container is elevated and the container exhaust is oriented towards a desired area, such as plants. The gases produced may be directed at plants for providing them with additional carbon dioxide. Further, the subsequent mushrooms may be dispersed to help decompose wood, soil, and also to increase the available nutrient profile in the soil.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 1 depicts a cross-sectioned side perspective view of an exemplary vessel containing a spawn substrate, in accordance with the present invention;

FIG. 2 depicts an elevated perspective view of an exemplary sealing device in accordance with the present invention;

FIG. 3 depicts an elevated perspective view of an exemplary seal being cut to mix a spawn substrate with a production substrate, in accordance with the present invention;

FIG. 4A depicts an elevated perspective view of an exemplary seal being cut to mix a spawn substrate with a production substrate, in accordance with the present invention;

FIG. 4B depicts a side-elevated perspective view of an exemplary dispersion container in accordance with the present invention;

FIG. 4C depicts a lower perspective view of an exemplary dispersion container in accordance with the present invention;

FIG. 5 depicts an elevated perspective view of an exemplary system for producing fungi for use in ecosystem dispersing a fungi byproduct on an exemplary ecosystem, in accordance with the present invention; and FIG. 6 illustrates a flowchart diagram of an exemplary method for producing fungi for use in an ecosystem, in accordance with the present invention.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

FIGS. 1 through 6 are detailed perspective views of an exemplary system and method for producing fungi for use in ecosystem and the environment, in accordance with the present invention.

In the present invention, a system and method for producing fungi for an ecosystem efficiently, and in a novel manner, produces fungi and fungi byproducts 500 for use in the ecosystem 502. The system and method comprise chiefly of: 1) a production substrate 104 that serves as a growth medium; 2) a spawn substrate 108 for colonizing the fungi; and 3) a fungi culture 110 that inoculates the spawn substrate 108 for subsequent colonization of the fungi throughout the substrate mixture. The system and method may be utilized for segregating the production substrate 104 from the spawn substrate 108 in a vessel 100, and then combining them at a desired time and place to produce fungi and fungi byproducts 500 for dispersion into the ecosystem 502.

In one embodiment of the present invention, a production substrate 104 and a spawn substrate 108 combine in the vessel 100 to cultivate fungi and fungi byproducts 500 (FIG. 1). The substrates 104, 108 are segregated in the same vessel 100 and then combined on demand for production of fungi and fungi byproducts 500. The vessel 100 may include, without limitation, a polyethylene bag that at least partially allows light to pass through. The fungi and fungi byproducts 500 disperse towards the ecosystem through a dispersion container 400 that holds the vessel 100. The dispersion container 400 may include, without limitation, a cardboard box that is sized and dimensioned to contain the vessel 100 and the substrates 104, 108.

The dispersion container 400 comprises a container exhaust 402 for allowing the fungi byproducts 500, or a portion of the vessel 100 to at least partially pass through, whereby a portion of the vessel 100 passes through the container exhaust 402 to disperse the fungi byproducts 500. The container exhaust 402 may include a slit in a bottom surface of the dispersion container 400. The fungi byproducts 500 disperse from the vessel 100 through a vessel exhaust 202, such as a mesh or webbed aperture that is sized to release gases and extraneous liquids. The vessel exhaust 202 passes through the container exhaust 402. Those skilled in the art, in light of the present teachings, will recognize that gases such as carbon dioxide have greater mass than other gases, and therefore will disperse down onto the ecosystem 502 more readily than lighter gases. The vessel exhaust 202 should be directed downwardly, or towards a desired area of the ecosystem 502 to maximize dispersion of the carbon dioxide.

Those skilled in the art, in light of the present teachings, will recognize that the system and method for producing fungi for use in an ecosystem may be useful for the following: postponed inoculation of mushroom kits, commercial mushroom production, mold production, fungi research systems, natural carbon dioxide, methane, or other gas generator, educational biological composting kits, selective culture composting kits, bioremediation vessels, commercial spawn production.

In one embodiment of the present invention, the system for production of fungi for use in ecosystem utilizes containers and substrates in a novel manner. For example, without limitation, the production substrate 104 and the spawn substrate 108 are initially prepared and sterilized. The production substrate 104, which provides a growth medium, may include a combination of at least the following: dry rye grains, sawdust, coffee grinds, and straw. However, in other embodiments, additional ingredients may be utilized.

For example, without limitation, formation of the production substrate 104 may utilize used coffee grinds mixed with select hardwood sawdust at a 4 quart to 5 pound ratio. The material is mixed homogeneously while dry, and then 2 gallons of hot tap water are added to this and mixed homogeneously. This creates a production substrate 104 with a perfect moisture percentage and overall texture. After achieving the appropriate mix, the production substrate 104 is hydrated, placed in a colander, allowed to drain excess moisture, and then set aside. The spawn substrate 108 may be substantially similar to the production substrate 104 in composition and preparation, differentiating only at a later step when a fungi culture 110 is added for inoculation.

In some embodiments, each substrate 104, 108 is segregated into a section of the vessel 100 to prevent premature cultivation, thereby providing a longer shelf life. The shelf life may be 30-60 days. The production substrate 104 is sealed in a first vessel section 102, while the spawn substrate 108 is sealed in a second vessel section 106 (FIG. 2). A sealing device 204 uses mechanical, kinetic, or physical means to segregate the various sections of the vessel 100 into their appropriate section. In one embodiment, the sealing device 204 utilizes a seal 112 that can be easily removed, yet still forms secure closure, such as high heat resistant vinyl stretch bands.

In one embodiment, the vessel 100 that contains the production substrate 104, and in some embodiments, the spawn substrate 108 is sterilized in an autoclave. Those skilled in the art, in light of the present teachings, will recognize that fungi cultivation, and the substrates that produce fungi, are susceptible to contaminants, which may destroy the product. For example, without limitation, the vessel 100 may be sterilized in an autoclave for 3-4 hours at 256° Fahrenheit at a pressure of 15 psi.

In one embodiment, the production substrate 104 and the spawn substrate 108 are sterilized together. However, the spawn substrate 108 is sterilized only prior to being inoculated by the fungi culture 110. In this manner, the cultivation of the spawn substrate 108 is not denigrated by the sterilization process. However, in one alternative embodiment, only the production substrate 104 is sterilized, whereby the sterilization process occurs before the spawn substrate 108 is filled into the vessel 100.

The spawn substrate 108 is inoculated with a fungi culture 110, which may include, without limitation, spores, chopped up mushroom mycelium, and blended mushrooms. Those skilled in the art will recognize that the shelf life commences at this point, as the fungi culture 110 commences colonization in the spawn substrate 108. After inoculation, the vessel is stored at ambient room temperature not exceeding 90° Fahrenheit and not dropping below 50° Fahrenheit until the spawning substrate is completely colonized by the fungi culture 110. However, the larger colonization does not commence until the spawn substrate 108 mixes with the production substrate 104.

In one embodiment, the inoculation may occur through a syringe. For example, without limitation, a hypodermic syringe filled with an aqueous solution of suspended pure fungi culture 110 is hydraulically delivered into the second vessel section 106 containing sterile spawning substrate via a minute penetration made by the syringe that is subsequently patched upon removal of the needle by a small piece of clear tape. Alternatively autoclave vessels with self-healing injection ports can be used for liquid culture inoculations. After inoculating the spawn substrate 108 with the fungi culture 110, the production substrate 104 and the spawn substrate 108 may be combined any time thereafter to initiate the cultivation of the fungi.

The seal 112 between the substrates is broken. In one embodiment, the seal 112 may include a polyphenylene sulfide plastic zip tie, and may be cut with scissors or a knife. After the seal 112 is broken, the production substrate 104 in the first vessel section 102 mixes with the spawn substrate 108 in the second vessel section 106, as referenced in FIG. 3. The system can be formed into a more effective shape and compactness for enhancing the colonization of the fungi. For example, without limitation, a rubber band is removed and the spawning substrate is mixed with the production substrate 104 as evenly as possible without potentially compromising the permanent hermetic seal. The loose material is then gently recompressed from the exterior of the vessel 100 into a brick shape.

The vessel 100 is placed inside the dispersion container 400, which is configured to cultivate and enhance the production of the fungi. As referenced in FIGS. 4A and 4B, the dispersion container 400 may include, without limitation, a cardboard box with a container exhaust 402 in the bottom surface. The dispersion container 400 does not allow light to pass through during the colonization process. Those skilled in the art, in light of the present teachings, will recognize that fungi grow more efficiently in the dark. In some embodiments, the dispersion container 400 includes a container exhaust 402, such as a slot, that allows the vessel exhaust 202 to pass through. The vessel exhaust 202 is pulled through the slot to disperse the fungi byproducts 500.

Figure 5:
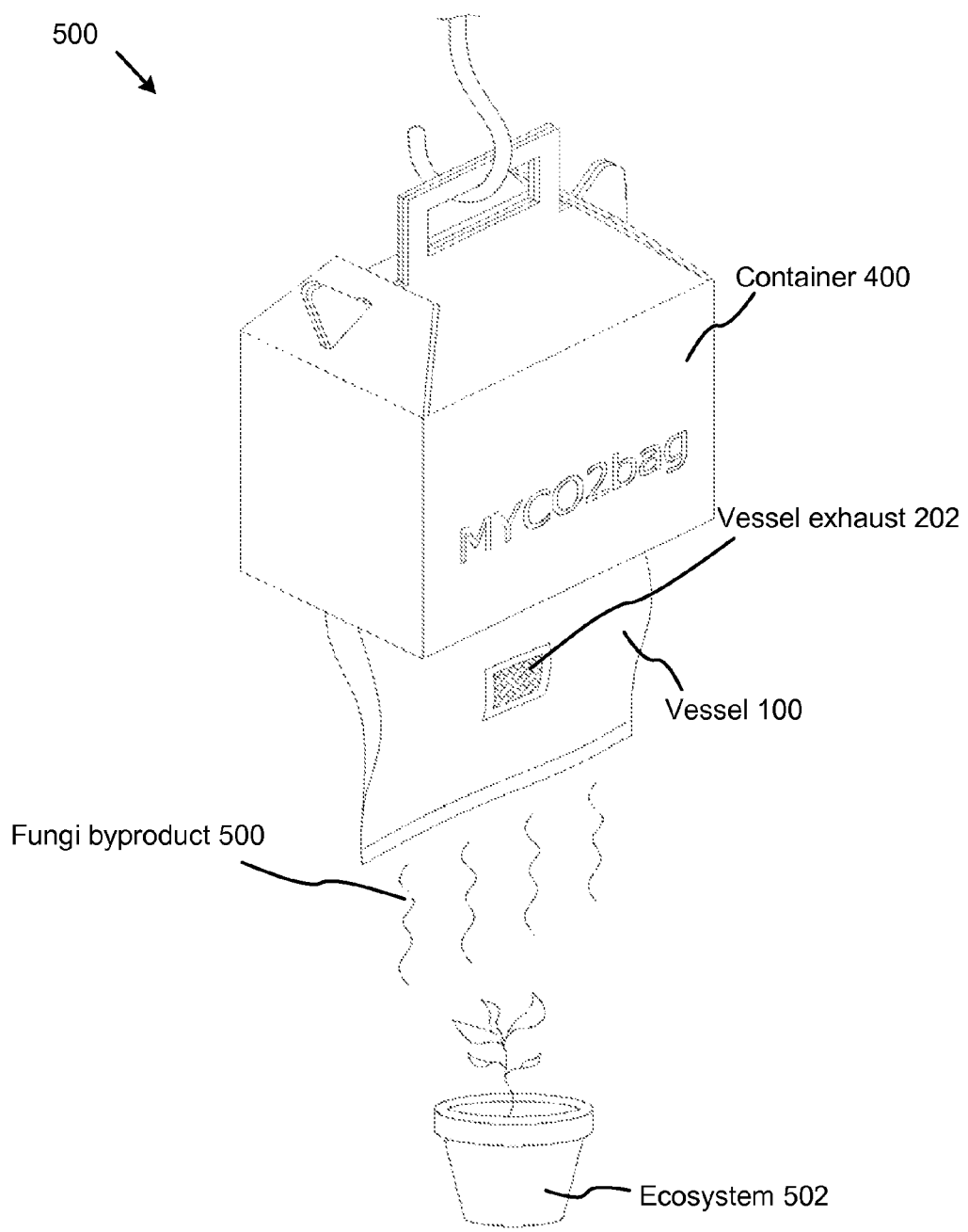

As reference din FIG. 5, the dispersion container 400 is oriented to disperse the fungi and fungi byproducts 500 onto the ecosystem 502. For example, without limitation, the dispersion container 400 is closed and hung in an elevated area over ecosystem 502, such that carbon dioxide, being heavier than oxygen, falls onto the ecosystem 502; thereby increasing the efficiency of gas delivery, reducing the fungi's exposure to light during the colonization period, and regulating and containing thermo genesis between ambient temperature fluctuations associated with night and day.

In one embodiment, after 15-30 days of carbon dioxide production, the vessel 100 can be removed from the dispersion container 400 and initiated into growing mushrooms by making a penetration in the vessel 100 where mushroom growth is desired, and placing it in an outside area and/or providing the correct environmental conditions to the approximate area the vessel 100 is stored as required to fruit mushrooms.

Furthermore, the fully colonized production substrate 104 can be broken apart by hand and placed on top the flattened dispersion container 400 for various agricultural uses, including, without limitation, creating outdoor mushroom patches, mixing with potting or garden soil to increase available nutrient profile, using as spawn to created homemade mushroom kits, using in environmental activism projects like bioremediation, and adding to a compost or yard waste garbage. In one embodiment, after full use, the vessel 100 can be cleaned inside and then dried before folding and placing it into a provided paid postage return envelope for reuse or proper recycling.

Those skilled in the art, in light of the present teachings, will recognize that the fungi and the fungi byproducts 500 provide great benefit to the ecosystem 502. For example, mushrooms serve as recyclers for wood and organic material. They are the only organisms that can digest the tough and fibrous lignin in wood, and make it available for other organisms. Further, mushroom cultivation spent substrate is very nutritive and improves the soil structure. As an additional benefit to the ecosystem 502, mushrooms can grow on waste, such as coffee ground or cardboard, and have strong soil remediation properties, such as decontaminating petroleum pollution.

FIG. 6 is a flowchart diagrams illustrating an embodiment of a method 600 for producing fungi for use in ecosystem, in accordance with the present invention. In a first embodiment, as referenced in FIG. 6, a method 600 for producing fungi for use in an ecosystem may include an initial Step 602 of preparing a production substrate 104. The production substrate 104 serves as a growth medium for cultivating and providing nutrients to the fungi. An eclectic assortment of ingredients are mixed and hydrated to form the appropriate production substrate 104. Suitable materials for producing the production substrate 104 may include, without limitation, dry rye grains, sawdust, coffee grinds, and straw. However, in other embodiments, additional ingredients may be utilized. After achieving the appropriate mix, the production substrate 104 is hydrated, placed in a colander, allowed to drain excess moisture, and then set aside. The spawn substrate 108 may be substantially similar to the production substrate 104 in system and preparation, differentiating in a later step when a fungi culture 110 is added for inoculation.

Next, the method comprises a Step 604 of filling a vessel 100 with the production substrate 104. The vessel 100 may include a polyurethane bag, or similar transparent or opaque bag that allows light to pass through, and comprises flexibility.

The method may then proceed to a Step 606 of sealing the vessel 100 with a sealing device 204 to form a first vessel section 102 for the production substrate 104. The vessel 100 may be mechanically, kinetically, or physically sealed to form the segregated first vessel section 102. In one embodiment, an impact seal 112 is utilized. In yet another embodiment, a heat resistant vinyl stretch band segregates the first vessel section 102 from the rest of the vessel 100.

The method then requires a Step 608 of preparing the spawn substrate 108. The spawn substrate 108 may be similar to the production substrate 104. Until the spawn substrate 108 is inoculated with spawn, such as spores and mushroom mycelium, the shelf life of the substrates for fungi cultivation cannot commence.

Next, the method comprises a Step 610 of filling the vessel 100 with the spawn substrate 108. The spawn substrate 108 does not mix with the production substrate 104 because the production substrate 104 is segregated in the first vessel section 102 of the vessel 100. The spawn substrate 108 positions on an opposite end of the vessel 100 from the production substrate 104.

A next Step 612 comprises sterilizing the vessel 100 with the substrate or substrates contained inside. Those skilled in the art, in light of the present teachings, will recognize that fungi cultivation, and the substrates that produce fungi, are susceptible to contaminants, which may destroy the product. The vessel 100 containing the production substrate 104 and the spawn substrate 108 is sterilized. However, in one alternative embodiment, the vessel 100 containing only production substrate 104 is sterilized, whereby the sterilization process occurs before the spawn substrate 108 is filled into the vessel 100. An autoclave or any other appropriate sterilization process may be utilized to sterilize the vessel 100.

A next Step 614 includes inoculating the spawn substrate 108 with a fungi culture 110, such as spores and fungi mycelium. The inoculation may utilize any inoculation procedure deemed acceptable or necessary per the growing parameters of the select fungi culture 110. Those skilled in the art will recognize that once inoculation of the spawn substrate 108 occurs, it is being colonized by the select fungi culture 110 creating a shelf life prior to the production substrate 104 being inoculated. In one embodiment, the vessel 100 may be stored at ambient room temperature not exceeding 90° Fahrenheit and not dropping below 50° Fahrenheit until the spawn substrate 108 is completely colonized by the fungi culture 110.

The method may then proceed to a Step 616 of hermetically sealing the vessel 100 around the spawn substrate 108 to form a second vessel section 106, separate from the production substrate 104. Likewith the first vessel section 102, the vessel 100 may be mechanically, kinetically, or physically sealed to form the segregated second vessel section 106. In one embodiment, a heat resistant vinyl stretch band segregates the second vessel section 106 from the first vessel section 102 and the rest of the vessel 100.

This naturally leads to a Step 618 of combining the production substrate 104 with the spawn substrate 108. The mechanical seal 112 or separator rubber band is removed and the spawn substrate 108 is mixed with the production substrate 104 as evenly as possible without potentially compromising the permanent hermetic seal 112. In some embodiments, the loose material of the substrate mixture may be gently recompressed from the exterior of the vessel 100 into a brick shape.

A next Step 620 includes colonizing the production substrate 104 with the spawn substrate 108. During colonization, the spawn substrate 108 begins to decompose the production substrate 104, drawing nutrients in the process. Additionally, if mushroom mycelium is utilized as the fungi culture 110, it consolidates its hold on the production substrate 104 by extending new strands of mycelium into the substrate mixture. The colonization produces fungi byproducts 500, including, without limitation, carbon dioxide, methane, nitrous oxide, liquids, and chemical extractions.

The method further comprises a Step 622 of placing the vessel 100 at least partially inside a dispersion container 400. The dispersion container 400 also inhibits light form entering the vessel 100 during colonization. In this manner, the dispersion container 400 serves as a dark, cool area for efficient growth of the fungi. Those skilled in the art will recognize that fungi grow more efficiently in the dark. Additionally, the dispersion container 400 includes a container exhaust 402, whereby gases from a vessel exhaust escapes 202.

A final Step 624 includes dispersing the fungi and the fungi byproducts 500 for the ecosystem 502. The ecosystem 502 may include, without limitation, agriculture, and the environment. The fungi byproducts 502 include carbon dioxide, which is heavier than oxygen, and therefore may be elevated to fall onto the ecosystem 502. After full cultivation, in one embodiment, the subsequent mushrooms may be dispersed to help decompose wood, soil, and also to increase the available nutrient profile in the soil. Additionally, the gases produced may be directed at plants for providing them with additional carbon dioxide.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for producing fungi, the method comprising:
preparing a production substrate;
filling a vessel with the production substrate;
sealing the production substrate in a first vessel section;
preparing a spawn substrate;
filling the vessel with the spawn substrate;
sterilizing the vessel;
inoculating the spawn substrate with a fungi culture;
sealing the spawn substrate in a second vessel section;
combining the production substrate and the spawn substrate;
colonizing the production substrate with the spawn substrate;
placing the vessel at least partially inside a dispersion container; and
dispersing the fungi and a fungi byproduct.

2. The method of claim 1, wherein the fungi comprises mushrooms.

3. The method of claim 1, wherein the production substrate comprises a mixture formed at least from a rye grains, and sawdust, and straw.

4. The method of claim 1, wherein the fungi culture comprises a mushroom mycelium.

5. The method of claim 1, wherein the vessel comprises a polyethylene bag.

6. The method of claim 1, wherein the dispersion container comprises a cardboard box sized and dimensioned to at least partially receive the vessel.

7. The method of claim 1, wherein the step of filling a vessel with the production substrate comprises placing the production substrate in a first vessel section.

8. The method of claim 1, wherein the step of sterilizing the vessel comprises utilizing an autoclave for 4 hours at 256 degrees Fahrenheit at a pressure of 15 pounds per square inch.

9. The method of claim 1, wherein the step of inoculating the spawn substrate with a fungi culture comprises utilizing a syringe filled with an aqueous solution of suspended pure fungi culture to hydraulically deliver the fungi culture into the second vessel section.

10. The method of claim 1, wherein the step of combining the production substrate and the spawn substrate cutting a seal between the first vessel section and the second vessel section.

11. The method of claim 1, wherein the step of dispersing the fungi and a fungi byproduct comprises at least partially extending a vessel exhaust through a container exhaust for directional dispersion of the fungi byproduct.

12. The method of claim 1, wherein the step of sterilizing the vessel precedes the step of filling the vessel with the spawn substrate.

13. A system for producing fungi, the system comprising: a production substrate, the production substrate provides a growth medium for growing fungi; a spawn substrate, the spawn substrate colonizes the fungi, the spawn substrate further receives a fungi culture; a vessel, the vessel contains the production substrate in a first vessel section, the vessel further contains the spawn substrate in a second vessel section, the vessel comprising a vessel exhaust for dispersing a fungi byproduct; a sealing device, the sealing device segregates the vessel into the first vessel section and the second vessel section, the sealing device at least partially encloses a seal between the first vessel section and the second vessel section; and a dispersion container, the dispersion container at least partially receives the vessel, the dispersion container comprising a dispersion exhaust, the dispersion exhaust at least partially allows the vessel exhaust to pass through for dispersing the fungi byproduct on an ecosystem.

\* \* \* \* \*